United States Patent
Allee et al.

(10) Patent No.: US 7,850,651 B2
(45) Date of Patent: Dec. 14, 2010

(54) BONE MARROW ASPIRATION NEEDLE

(75) Inventors: Tyler Allee, Sheboygan, WI (US); James M. McKale, Leesburg, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 12/210,372

(22) Filed: Sep. 15, 2008

(65) Prior Publication Data

US 2010/0069843 A1    Mar. 18, 2010

(51) Int. Cl.
*A61M 5/178* (2006.01)
*A61M 25/00* (2006.01)

(52) U.S. Cl. .................. 604/164.01; 604/164.04; 604/264

(58) Field of Classification Search .......... 604/264, 604/164.01–167.06, 170.03, 167–185
See application file for complete search history.

(56) References Cited

U.S. PATENT DOCUMENTS

| | | | |
|---|---|---|---|
| 2,850,007 A * | 9/1958 | Lingley | 600/567 |
| 3,893,445 A | 7/1975 | Hofsess | |
| 4,469,109 A | 9/1984 | Mehl | |
| 4,763,667 A * | 8/1988 | Manzo | 600/563 |
| D320,857 S | 10/1991 | Tompkins et al. | |
| 5,334,160 A * | 8/1994 | Ellis | 604/167.03 |
| 5,522,398 A | 6/1996 | Goldenberg et al. | |
| D379,515 S | 5/1997 | Kuehn et al. | |
| 5,634,473 A | 6/1997 | Goldenberg et al. | |
| 5,807,277 A | 9/1998 | Swaim | |
| D436,664 S | 1/2001 | Lamoureux | |
| 6,312,394 B1 | 11/2001 | Fleming, III | |
| 6,478,751 B1 | 11/2002 | Krueger et al. | |
| 6,755,793 B2 | 6/2004 | Lamoureux et al. | |
| 6,849,051 B2 | 2/2005 | Sramek et al. | |
| 7,081,123 B2 | 7/2006 | Merboth et al. | |
| 7,179,232 B2 | 2/2007 | Sutton et al. | |
| 2003/0225364 A1 | 12/2003 | Kraft et al. | |
| 2004/0153005 A1 | 8/2004 | Krueger | |
| 2004/0191897 A1 | 9/2004 | Muschler | |

(Continued)

OTHER PUBLICATIONS

"Announcing the improved BioAccess Bone Marrow Collection System," web page from BioAccess web site http://www.bioaccess.com/collection_system.htm (2004). Applicants also note that this link was received in an e-mail at least as early as Nov. 8, 2007.

(Continued)

*Primary Examiner*—Nicholas D Lucchesi
*Assistant Examiner*—Rebecca E Eisenberg
(74) *Attorney, Agent, or Firm*—Harness, Dickey

(57) ABSTRACT

An aspiration assembly including an outer cannulated needle having a tip, a threaded collar, and an inner aspiration needle. The threaded collar is mounted to an end of the outer cannulated needle opposite to the tip. The inner aspiration needle has a tip at a first end and a threaded portion proximate to a second end. The inner aspiration needle is inserted within the outer cannulated needle such that the tip of the inner aspiration needle extends beyond the tip of the outer cannulated needle and the threaded portion of the inner aspiration needle threadably engages the threaded collar. The distance that the tip of the inner aspiration needle extends from the tip of the outer cannulated needle increases when the inner aspiration needle is rotated in a first direction relative to the outer cannulated needle.

30 Claims, 7 Drawing Sheets

U.S. PATENT DOCUMENTS

| | | | |
|---|---|---|---|
| 2004/0267154 A1* | 12/2004 | Sutton et al. | ................ 600/562 |
| 2007/0154460 A1 | 7/2007 | Kraft et al. | |
| 2007/0197996 A1 | 8/2007 | Kraft et al. | |
| 2007/0198043 A1 | 8/2007 | Cox et al. | |
| 2007/0276402 A1 | 11/2007 | Frankel et al. | |
| 2008/0015467 A1 | 1/2008 | Miller | |
| 2008/0015468 A1 | 1/2008 | Miller | |

OTHER PUBLICATIONS

"Aspiration/Biopsy," web page from CardinalHealth web site http://www.cardinal.com/us/en/distributedproducts/index.asp?cat=surgerycenter&ID=Surgery%20Center%20Products;Needles%20-%26%20Syringes;Aspiration%2fBiopsy;. Applicants also note that this link was received in an e-mail at least as early as Nov. 8, 2007.
"BD Medical Product Catalog," Section Listing A through R (Jan. 1, 2006) Becton, Dickinson and Company.
"Bierman Needle," order page from Dyna Medical Corp. web site http://www.dynamedical.com/pg3h.html (copyright 1999) accessed Jun. 23, 2010. Applicants also note that this link was received in an e-mail at least as early as Nov. 8, 2007.
"Bone Marrow Aspiration Needle with Adjustable Depth Stop," order page from MEDEX web site http://www.medexinternational.com/htm/bone2.html which is copyrighted 2004. Applicants also note that this link was received in an e-mail at least as early as Nov. 8, 2007.
"Bone Marrow Aspiration Needle," Marrowgauge™ Needles, Needles & Syringes catalogue, Rocketmedical—while the catalogue is undated, utilizing the Internet Archive Wayback Machine service, Applicant determined the catalogue appears to have first appeared on the company's web site (www.rocketmedical.com) sometime between Aug. 2004 and Oct. 2004.
"Bone Marrow Biopsy Needles—Medical Supplies, Baxter Allegiance," order page from Quality Medical Supplies, http://www.qualitymedicalsupplies.com/page/QMS/CTGY/SN-BM, 2 pages. Applicants also note that this link was received in an e-mail at least as early as Nov. 8, 2007.
"Bone Marrow Biopsy System, The Single Entry Biopsy Solution, J-style Needle & Marrow Low™ device, plus I-style Aspiration Needle," brochure, (2004) US Biopsy™, a division of Promex Technologies, LLC, 3 pages.
"Bone Marrow Transplantation Bone Marrow Transplantation Set," brochure, 1 page, H.S. Medical, Inc. (while the brochure is undated, an illustration of the needle appears on the company's web site which is copyrighted 2008 at http://www.hshospitalservice.com//prod.php?id=105—1 page was accessed Jun. 22, 2010). Applicants also believe that the brochure existed at least as early as Nov. 8, 2007 based upon receiving this as an attachment to an e-mail received on that date.
"Bone/Bone Marrow Biopsy Set with Extraction Cannula," brochure/order page from MEDEX web site http://www.medexinternational.com/htm/bone.html which is copyrighted 2004. Applicants also note that this link was received in an e-mail at least as early as Nov. 8, 2007.
"Diagnostic Procedure Trays," brochure (2004) Busse Hospital Disposables, pp. 1-12.
"Hummingbird Ultra-Precision Procedural Needles, Aspircore™ All-in-one Bone Marrow Biopsy System, 'J' and 'I' Bone Marrow Biopsy Needles" brochure, World Wide Medical Technologies, 2 pages—while the brochure is undated, Applicants were able to view an illustration of the products at the company's web site at <http://www.wwmedtech.com/bm.php>, which is copyrighted 2007 and which Applicants accessed on Jun. 22, 2010.
"I type Needle—Illinois Sternal/Iliac Bone Marrow Aspiration," order page from Dyna Medical Corp. web site http://www.dynamedical.com/pg33w.html (copyright 1999) accessed Jun. 23, 2010. Applicants also note that this link was recieved in an e-mail at least as early as Nov. 8, 2007.
"Ignite® Power Mix, Injectable Stimulus for Fracture Callus Formation," Surgical Technique, Wright Medical Technology, Inc., (2006) 4 pages.

"Illinois Sternum/Iliac Aspiration Needle," order page from Dyna Medical Corp. web site http://www.dynamedical.com/pg3i.html (copyright 1999) accessed Jun. 23, 2010. Applicants also note that this link was received in an e-mail at least as early as Nov. 8, 2007.
"Intravention Radiology," order pages (4) from IskusHealth web site, http://www.pharmalink.ie/catalogue/default.asp?catid=16&itemID=29. Applicants also note that this link was received in an e-mail at least as early as Nov. 8, 2007.
"J type Needle—Bone Marrow Biospy Aspiration," order page from Dyna Medical Corp. web site http://www.dynamedical.com/pg333a.html (copyright 1999) accessed Jun. 23, 2010. Applicants also note that this link was received in an e-mail at least as early as Nov. 8, 2007.
"Large Silverman Needle," order page from Dyna Medical Corp. web site http://www.dynamedical.com/pg33m.html (copyright 1999) accessed Jun. 23, 2010. Applicants also note that this link was received in an e-mail at least as early as Nov. 8, 2007.
"Medax Products/Biopsy CAGE, Bone Marrow Aspiration Needle," brochure, (2003) Medax® Medical Devices, 3 pages.
"Medical Products ISO 9001:2007 ISO13485," catalog, pp. 1-20, directed to pp. 8-13 (2008) Cadence Science.
"MIS™ Sterile Services Range," brochure, Issue 1, (Nov. 2005) pp. 17-20, Rocket Medical.
"Neo Oxus® Bone Marrow Biopsy and Aspiration Needle, " brochure, Medax® medical devices (Nov. 2003) 2 pages.
"Osgood Needle," order page from Dyna Medical Corp. web site http://www.dynamedical.com/pg3j.html (copyright 1999) accessed Jun. 23, 2010. Applicants also note that this link was received in an e-mail at least as early as Nov. 8, 2007.
"Oxus® Bone Marrow Biopsy and Aspiration Needle, " brochure, Medax® medical devices (Nov. 2003) 2 pages.
"Perfectus® Bone Marrow Aspiration Needle with Adjustable Needle Stop, " brochure, Medax® medical devices (Nov. 2003) 2 pages.
"Ranfac's Bone Marrow Biopsy Needles, Godenberg SNARECOIL™ Needle, I-Type Bone Marrow Aspiration Needle, Bone Marrow Procedure Tray," brochure, 4 pages (undated). Applicants also believe that the brochure existed at least as early as Nov. 8, 2007 based upon receiving this as an attachment to an e-mail received on that date.
"Rosenthal Needle," order page from Dyna Medical Corp. web site http://www.dynamedical.com/pg3a.html (copyright 1999) accessed Jun. 23, 2010. Applicants also note that this link was received in an e-mail at least as early as Nov. 8, 2007.
"Snarecoil* Making the twists and turns of bone marrow biopsy ancient history," brochure, (2003) Tyco Healthcare Group Kendall, 2 pages.
"Specialty Procedure Needles," catalogue, 38 pages, directed to pp. 11B-24B, Popper® & Sons, Inc.—while the catalogue is undated, Applicants were able to access and view the catalogue by utilizing the Internet Archive Wayback Machine, selecting the last date the web site existed (May 26, 2008) at http://web.archive.org/web/20060623134646/popperandsons.com/pdf/ib_specialty.pdf; Popper & Sons' original web site now redirects to <http://www.cadencescience.com/> (the new catalogue as it appears on the new website has also been cited). Applicants also believe that the brochure existed at least as early as Nov. 8, 2007 based upon receiving this as an attachment to an e-mail received on that date.
"Vitoss® Bone Marrow: A validated biologic driver for bone regeneration," Bone Marrow Aspirate, brochure, Orthovita, Inc., (2008) 1 page.
"Vitoss® Imbibe—Advanced Bullet-Tip Needle Design," Bone Marrow Aspirate, brochure, Orthovita (2007) 1 page.
"Westerman Jensen Needle," order page from Dyna Medical Corp. web site http://www.dynamedical.com/pg3g.html (copyright 1999) accessed Jun. 23, 2010. Applicants also note that this link was received in an e-mail at least as early as Nov. 8, 2007.
Gallini Medical Devices brochure: "Biomid Bone Marrow Aspiration Biopsy Needle," p. 16, designated as 9999-058(date Jan. 2006) REV01. "Biosystem Bone Marrow Aspiration Biopsy Needle," p. 17, designated as 9999-059(date Jan. 2006) REV01. "Acri Bone Marrow Harvest Needle," p. 18, designated as 9999-060(date Jan. 2006) REV01. "Acri R Disposable Klima-Rosenthal Trocar Needle," p. 19, designated as 9999-061(date Jan. 2006) REV01. "Isan Sternal Iliac Aspiration Needle," p. 20, designated as 9999-062(date Jan. 2006) REV01. "Myelovac® The New Disposable Needle for Automatic Sternal Iliac Aspiration," p. 21, 9999-063(date Jan. 2006) REV01. "Myelo-Gal Disposable Paediatric Mallarmé Trocar Needle," p. 22, 9999-064(date Jan. 2006) REV01. "Myelo-Gal R Disposable Klima-Rosenthal Trocar Needle," p. 23, 9999-065(date Jan. 2006) REV01. Applicants also believe that the brochure existed at least as early as Nov. 8, 2007 based upon receiving this as an attachment to an e-mail received on that date.

\* cited by examiner

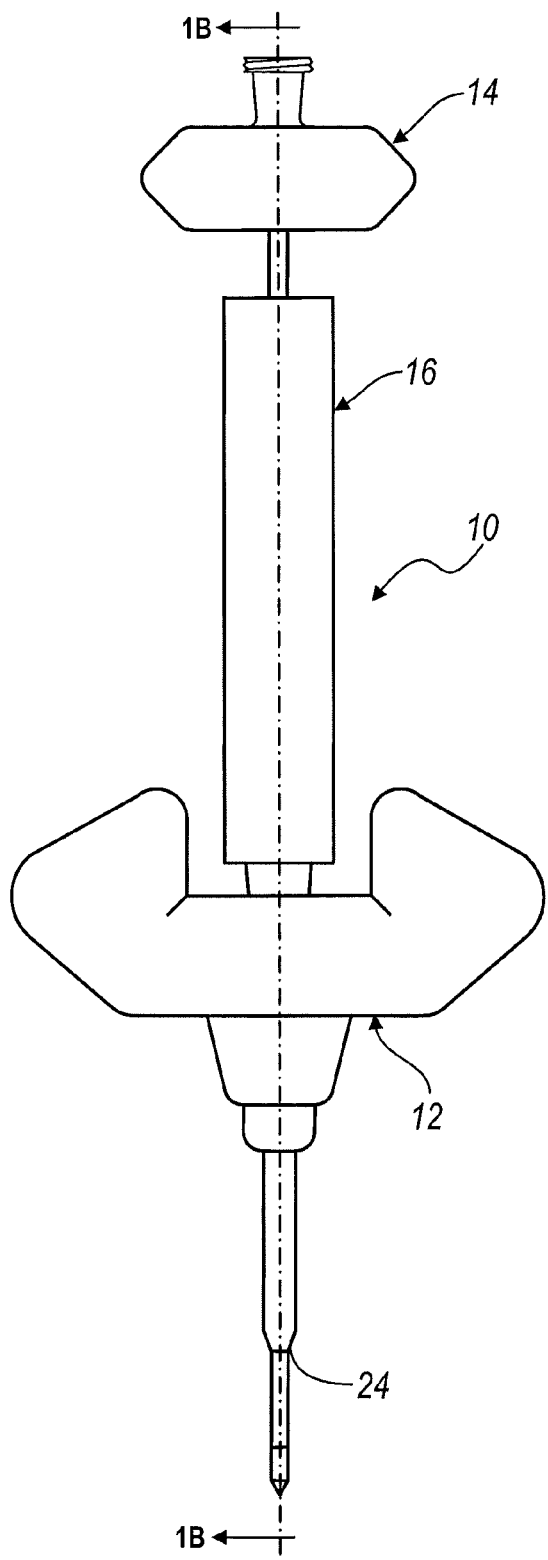
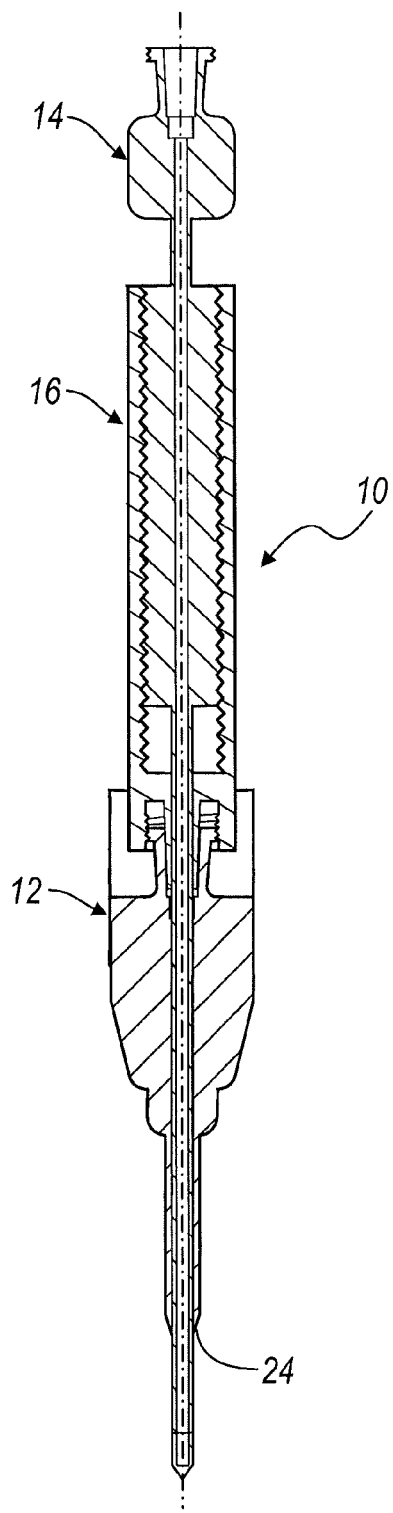
FIG. 1A
FIG. 1B

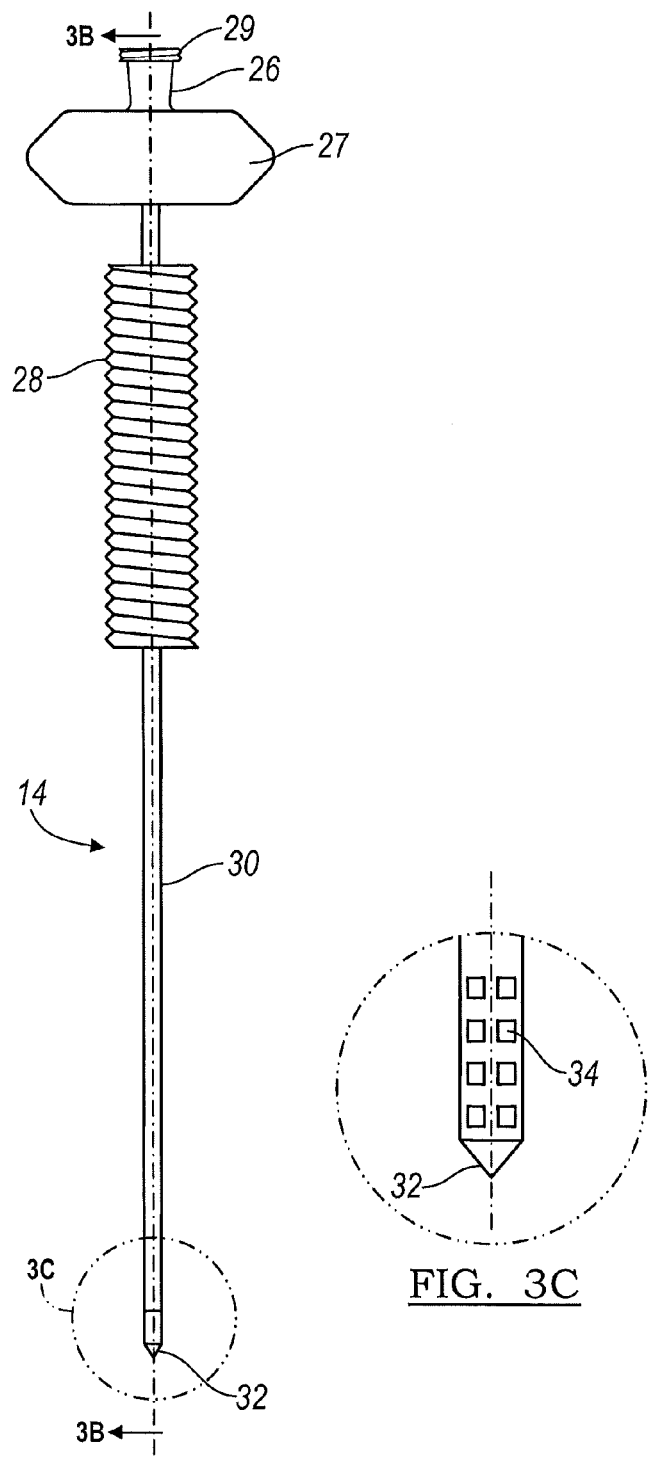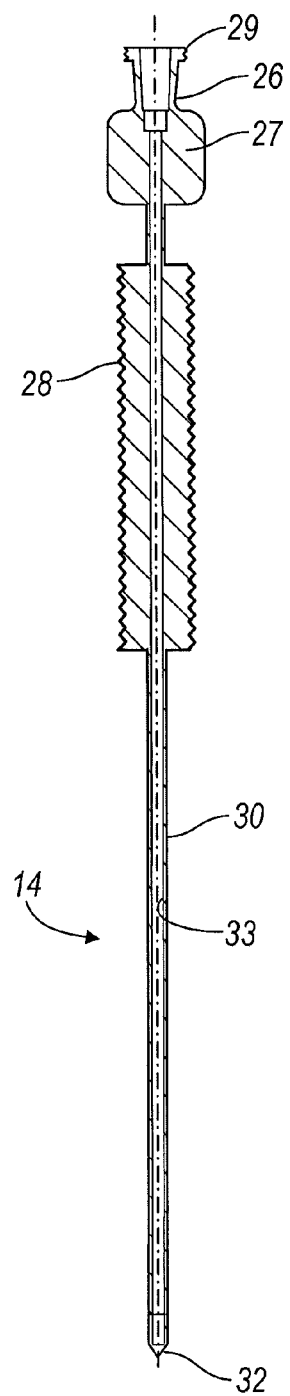
FIG. 3A FIG. 3C FIG. 3B

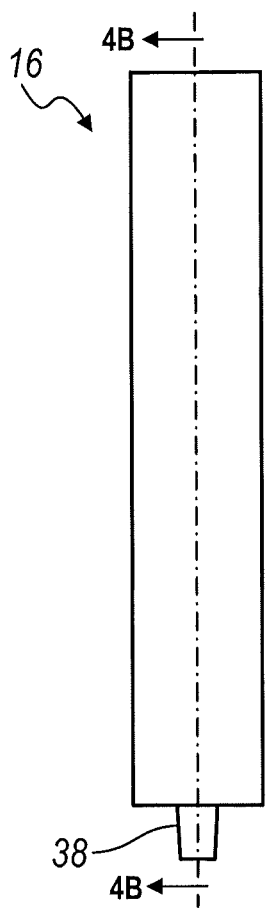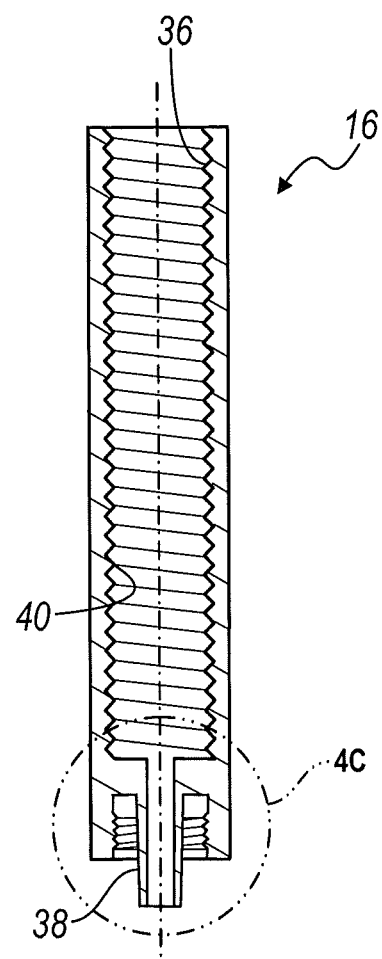
FIG. 4A
FIG. 4B
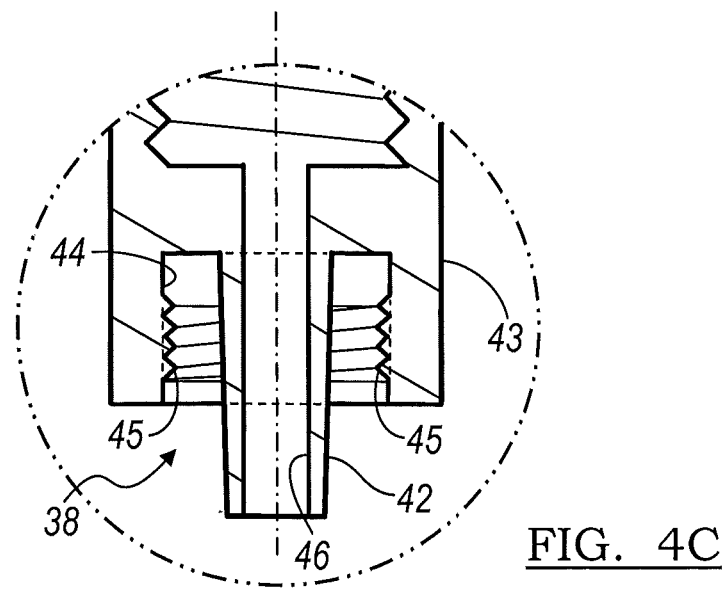
FIG. 4C

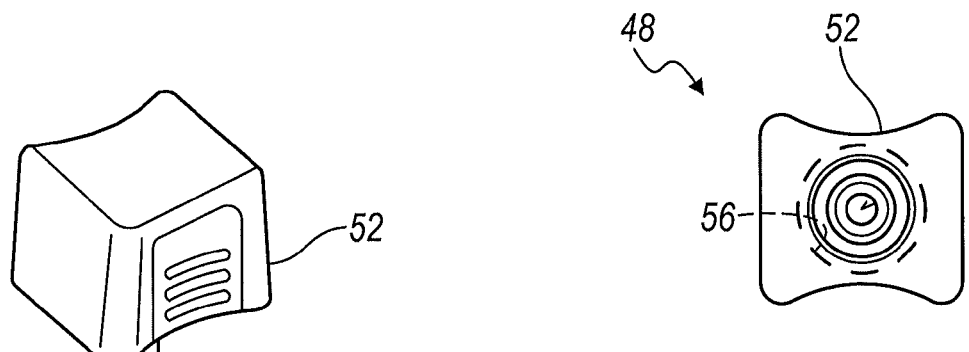
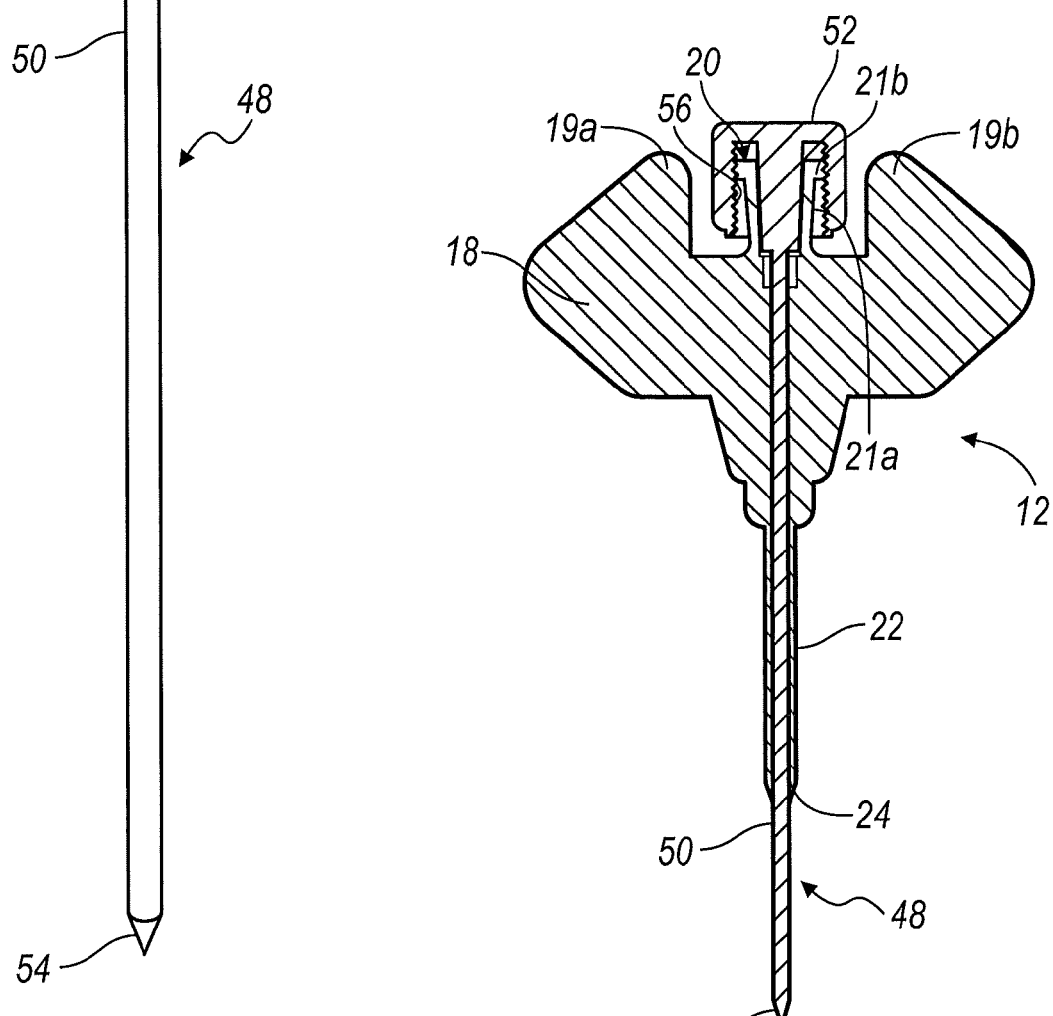
FIG. 5A
FIG. 5B
FIG. 6

US 7,850,651 B2

BONE MARROW ASPIRATION NEEDLE

FIELD

The present disclosure relates to methods and apparatuses for extracting biological materials. In particular, the present disclosure relates to methods and apparatuses for withdrawing bone marrow from bone.

BACKGROUND

The statements in this section merely provide background information related to the present disclosure and may not constitute prior art.

Bone marrow aspiration is a procedure used to obtain the blood-forming portion (marrow) of the inner core of bone for examination in a laboratory or for transplantation. The procedure often includes inserting a needle into a bone that contains marrow and withdrawing the marrow. When harvesting large amounts of bone marrow, such as about 55 ml, no more than 2-3 ml of bone marrow is generally taken at one time. Between each successive 2-3 ml draw, the needle is generally advanced into the marrow cavity further and rotated by 90°. The reason for this is that if too much bone marrow is drawn from one area, the sample can be diluted with peripheral blood. In a typical surgical environment, manually advancing and rotating the needle by 90° can be a cumbersome and time consuming process. Thus, there is a need for improved devices and methods for aspirating bone marrow from bone, as well as aspirating biological components generally.

SUMMARY

The present teachings provide for an aspiration assembly including an outer cannulated needle having a tip, a threaded collar, and an inner aspiration needle. The threaded collar is mounted to an end of the outer cannulated needle opposite to the tip. The inner aspiration needle has a tip at a first end and a threaded portion proximate to a second end. The inner aspiration needle is inserted within the outer cannulated needle such that the tip of the inner aspiration needle extends beyond the tip of the outer cannulated needle and the threaded portion of the inner aspiration needle threadably engages the threaded collar. The distance that the tip of the inner aspiration needle extends from the tip of the outer cannulated needle increases when the inner aspiration needle is rotated in a first direction relative to the outer cannulated needle. The distance that the tip of the inner aspiration needle extends from the tip of the outer cannulated needle decreases when the inner aspiration needle is rotated in a second direction relative to the outer cannulated needle. The second direction is opposite to the first direction.

The present teachings further provide for an aspiration assembly including an outer cannulated needle having a needle tip and a handle, a collar having internal threads, and an inner aspiration needle. The inner aspiration needle has a tip at a first end, a threaded portion proximate to a second end, and a needle portion between the tip of the inner aspiration needle and the second end of the inner aspiration needle. A rigid stylet has a tip at a first end, an interlocking device at a second end, and a needle portion extending between the tip of the stylet and the interlocking device. The assembly includes a first configuration in which the rigid stylet mates with one of the outer cannulated needle or the collar such that the interlocking device of the rigid stylet is attached to one of the handle or the collar. The needle portion of the stylet extends through the needle tip of the outer cannulated needle. The tip of the rigid stylet extends beyond the needle tip of the outer cannulated needle. The assembly includes a second configuration in which the collar is mounted to the handle of the outer cannulated needle. The inner aspiration needle is connected to the collar through cooperation between the internal threads of the collar and the threaded portion of the inner aspiration needle. The needle portion of the inner aspiration needle extends through the needle tip of the outer cannulated needle. The tip of the inner aspiration needle extends beyond the needle tip of the outer cannulated needle.

The present teachings further provide for a method for aspirating bone marrow from bone. The method includes the following: inserting a rigid stylet through an outer cannulated needle such that a stylet tip of the rigid stylet extends beyond a needle tip of the outer cannulated needle; inserting the rigid stylet and the outer cannulated needle through a bone cortex and into a bone marrow cavity; withdrawing the rigid stylet from the bone; connecting an inner aspiration needle to a collar having internal threads mounted to the outer cannulated needle such that a needle portion of the inner aspiration needle extends through the needle tip of the outer cannulated needle and a threaded portion of the inner aspiration needle threadably engages the internal threads of the collar; aspirating a first quantity of bone marrow from the bone marrow cavity through ports in a tip portion of the inner aspiration needle; rotating the inner aspiration needle in a first direction relative to the outer cannulated needle to move the inner aspiration needle from a first position in the bone marrow cavity to a second position in the bone marrow cavity; and aspirating a second quantity of bone marrow from the bone marrow cavity through the inner aspiration needle with the inner aspiration needle in the second position, the depth of the inner aspiration needle in the bone marrow cavity when in the first position is different from the depth of the inner aspiration needle in the bone marrow cavity when in the second position.

The present teachings also provide for an aspiration assembly including an outer cannulated needle, a collar, an inner aspiration needle, and a stylet. The outer cannulated needle has a needle tip and a handle. The collar has internal threads. The inner aspiration needle has an open tip at a first end, a connection device at a second end, a threaded portion proximate to the second end, and a needle portion between the tip of the inner aspiration needle and the second end of the inner aspiration needle. The stylet has a tip at a first end, an interlocking device at a second end, and a needle portion extending between the tip of the stylet and the interlocking device. The collar is mounted to the handle of the outer cannulated needle. The inner aspiration needle is connected to the collar through cooperation between the internal threads of the collar and the threaded portion of the inner aspiration needle. The needle portion of the inner aspiration needle extends through the needle tip of the outer cannulated needle. The tip of the inner aspiration needle extends beyond the needle tip of the outer cannulated needle. The stylet is connected to the inner aspiration needle through cooperation between the interlocking device of the stylet and the connection device of the inner aspiration needle. The needle portion of the stylet extends through the open tip of the inner aspiration needle and the tip of the stylet extends beyond the open tip of the inner aspiration needle.

The present teachings further provide for a method for aspirating bone marrow from bone. The method includes the following: connecting a collar having internal threads to an outer cannulated needle; connecting an inner aspiration needle to the collar such that a needle portion of the inner aspiration needle extends through a needle tip of the outer cannulated needle and a threaded portion of the inner aspiration needle threadably engages the internal threads of the collar; connecting a stylet to the inner cannulated needle such that a needle portion of the stylet extends through a needle tip of the inner cannulated needle; penetrating a bone marrow cavity of a bone using the stylet such that the stylet, inner aspiration needle, and the outer cannulated needle are seated within the bone; removing the stylet from cooperation with the inner cannulated needle and from within the bone; aspirating a first quantity of bone marrow from the bone marrow cavity through the inner aspiration needle; rotating the inner aspiration needle in a first direction relative to the outer cannulated needle to move the inner aspiration needle from a first position in the bone marrow cavity to a second position in the bone marrow cavity; and aspirating a second quantity of bone marrow from the bone marrow cavity through the inner aspiration needle with the inner aspiration needle in the second position, the depth of the inner aspiration needle in the bone marrow cavity when in the first position is different from the depth of the inner aspiration needle in the bone marrow cavity when in the second position.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1A is a side view of an aspiration needle assembly according to the present teachings;

FIG. 1B is a cross-sectional view of the aspiration needle assembly of FIG. 1A taken along line 1B;

FIG. 3A is a side view of an inner aspiration needle of the needle assembly of FIGS. 1A and 1B;

FIG. 3B is a cross-sectional view of the inner aspiration needle of FIG. 3A taken along line 3B;

FIG. 3C is a close-up view of area 3C of FIG. 3A;

FIG. 4A is a side view of a threaded collar of the aspiration needle assembly of FIGS. 1A and 1B;

FIG. 4B is a cross-sectional view of the threaded collar of FIG. 4A taken along line 4B of FIG. 4A;

FIG. 4C is a close-up view of area 4C of FIG. 4B;

FIG. 5A is a perspective view of a stylet according to the present teachings for use with the needle assembly of FIGS. 1A and 1B;

FIG. 5B is an end view of the stylet of FIG. 5A;

FIG. 6 is a cross-sectional view of the stylet in cooperation with the outer aspiration needle;

DETAILED DESCRIPTION

Figure 2A:
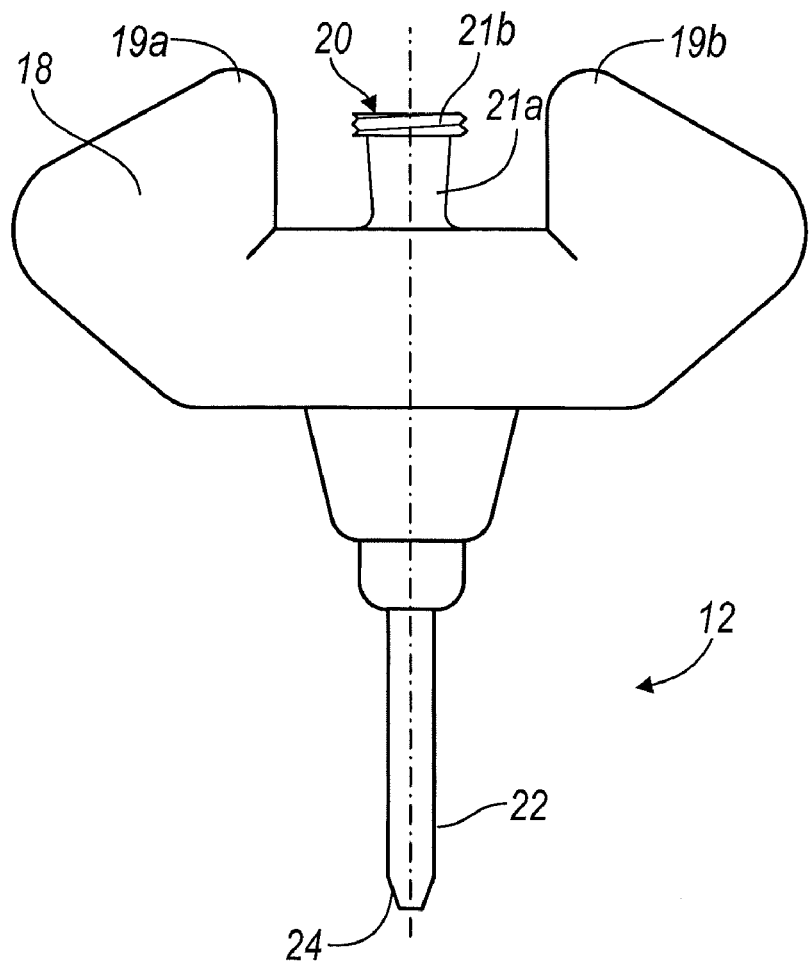
FIG. 2A is a side view of an outer aspiration needle of the needle assembly of FIGS. 1A and 1B.

The following description is merely exemplary in nature and is not intended to limit the present disclosure, application, or uses.

With initial reference to FIGS. 1A and 1B, an aspiration needle assembly according to the present teachings is illustrated at reference numeral 10. The aspiration needle assembly 10 generally includes an outer needle 12, an inner aspiration needle 14, and a threaded collar 16.

Figure 2B:
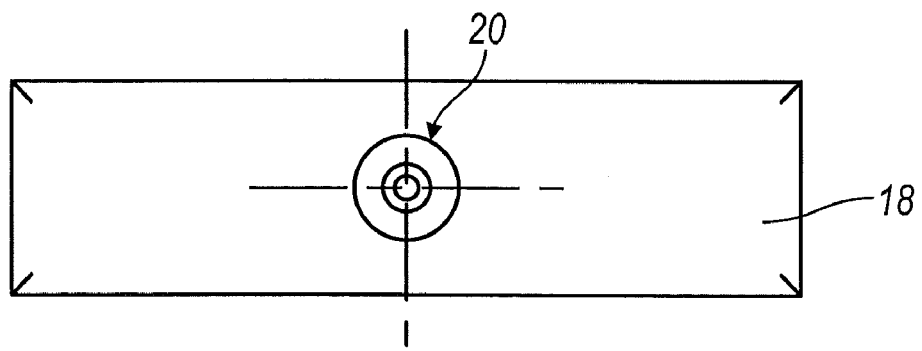
FIG. 2B is an end view of the outer aspiration needle of FIG. 2A.

With additional reference to FIGS. 2A and 2B, the outer needle 12 generally includes a handle 18, a female Luer lock 20, and a needle portion 22. The Luer lock 20 extends from a first end of the handle 18 and the needle portion 22 extends from a second end of the handle 18 that is opposite to the first end. The Luer lock 20 is recessed within the handle 18. The handle 18 includes winged portions 19a and 19b that are on opposite sides of the Luer lock 20. The Luer lock 20 can be any suitable type of device for fastening two components together. The Luer lock 20 includes a sidewall 21 having a first diameter portion 21a proximate to the handle 18 and a second diameter portion 21b that is distal to the handle 18. The second diameter portion 21b has external threads and has a diameter that is greater than the first diameter portion 21a. The needle portion 22 is cannulated and is in fluid communication with the female Luer lock 20 to permit passage of materials through the outer needle 12. The needle portion 22 has a pointed open tip 24. The pointed tip 24 can have any suitable shape, such as a conical tip having a sharpened end, as illustrated.

With additional reference to FIGS. 3A-3C, the inner aspiration needle 14 generally includes a female Luer lock 26, a handle portion 27, a threaded portion 28, and a needle portion 30 having a tip 32.

The female Luer lock 26 is at an end of the inner aspiration needle 14 that is opposite to the tip 32. The female Luer lock 26 can be any suitable fastening device for connecting the inner aspiration needle 14 to a syringe or other suitable device for withdrawing material through the inner aspiration needle 14. As illustrated, the female Luer lock 26 includes external threads 29.

The threaded portion 28 of the inner aspiration needle 14 is proximate to the female Luer lock 26. The threaded portion 28 is substantially cylindrical and includes an externally threaded sidewall. The tip 32 is conical and has a closed end. The tip 32 includes a plurality of ports 34 around its outer diameter to permit the passage of material into the inner aspiration needle 14. The ports 34 are spaced apart around the outer diameter of the tip 32 to permit intake of materials from an entire area encompassing the tip 32. The inner aspiration needle 14 is cannulated and includes a through bore 33 that provides for communication of material from the ports 34 through the inner aspiration needle 14 to the female Luer lock 26.

With additional reference to FIGS. 4A, 4B, and 4C, the threaded collar 16 defines an inner housing 36 and a male Luer lock 38. The inner housing 36 includes an inner threaded sidewall 40 in which the threads are sized and shaped to cooperate with the threaded portion 28 of the inner aspiration needle 14 to form an aspiration needle assembly 10 in which the distance that the tip 32 of the aspiration needle 14 extends from the tip 24 of the needle portion 22 of the handle 12 can be metered by rotation of the inner aspiration needle 14 within the threaded collar 16. The male Luer lock 38 includes a conical extending portion 42 and an outer skirt 43 that defines a recessed portion 44 therebetween. The recessed portion 44 receives the Luer lock 20 and includes threads 45 that cooperate with the threaded portion 21b of the female Luer lock 20 to enhance the connection between the male Luer lock 38 and the female Luer lock 20. A through port 46 extends through the extending portion 42 to the inner housing 36. One skilled in the art will recognize that the threaded collar 16 can be integral with the Luer lock 20 of the handle 12 or can be a separate part, as illustrated in FIGS. 4A, 4B, and 4C, which can securely mate with the Luer lock 20.

With additional reference to FIGS. 5A and 5B, a stylet or trocar is illustrated at reference numeral 48. The stylet 48 generally includes a needle portion 50 and an end cap 52. The needle portion 50 is rigid and solid and includes a pointed end 54. The end cap 52 is mounted to the stylet 48 at an end opposite to the pointed end 54. The end cap 52 includes a male Luer lock with threads 56 to permit the stylet 48 to be connected to the threaded portion 21b of the female Luer lock 20 of the outer needle 12, as illustrated in FIG. 6.

Use of the assembly 10 and the stylet 48 will now be described. The assembly 10 and the stylet 48 can be used for a variety of different purposes. For example and as described herein, the assembly 10 and the stylet 48 can be used to extract bone marrow from bone.

As illustrated in FIG. 6, the stylet 48 is mated with the outer needle 12 such that the needle portion 50 of the stylet 48 extends through the handle 18 and through the open tip 24 of the outer needle 12. The Luer lock threads 56 of the end cap 52 cooperate with the threaded portion 21b of the female Luer lock 20 of the handle 18 to secure the stylet 48 to the outer needle 12. When the threaded collar 16 is integral with the outer needle 12, the stylet 48 is inserted through the threaded collar 16 and provided with an extended length so that the pointed end 54 extends from the tip portion 24 of the outer needle 12. Further, the end cap 52 can be configured to mate with the end of the threaded collar 16 that is opposite to the Luer lock 38.

With the stylet 48 secured to the outer needle 12, the stylet 48 and the outer needle 12 are advanced into the bone cortex. The pointed end 54 of the stylet 48 protrudes out beyond the needle portion 22 of the outer needle 12 to make initial contact with the bone. The pointed end 54 has a sharp surface to facilitate insertion of the stylet 48 and the outer needle 12 into the bone. Thus, the rigid stylet needle portion 50 facilitates penetration of the bone and prevents bone and other materials from entering and clogging the tip portion 24 of the outer needle 12. The stylet 48 and the handle 12 are advanced into the bone marrow cavity to a point where bone marrow can be aspirated.

Figure 7A:
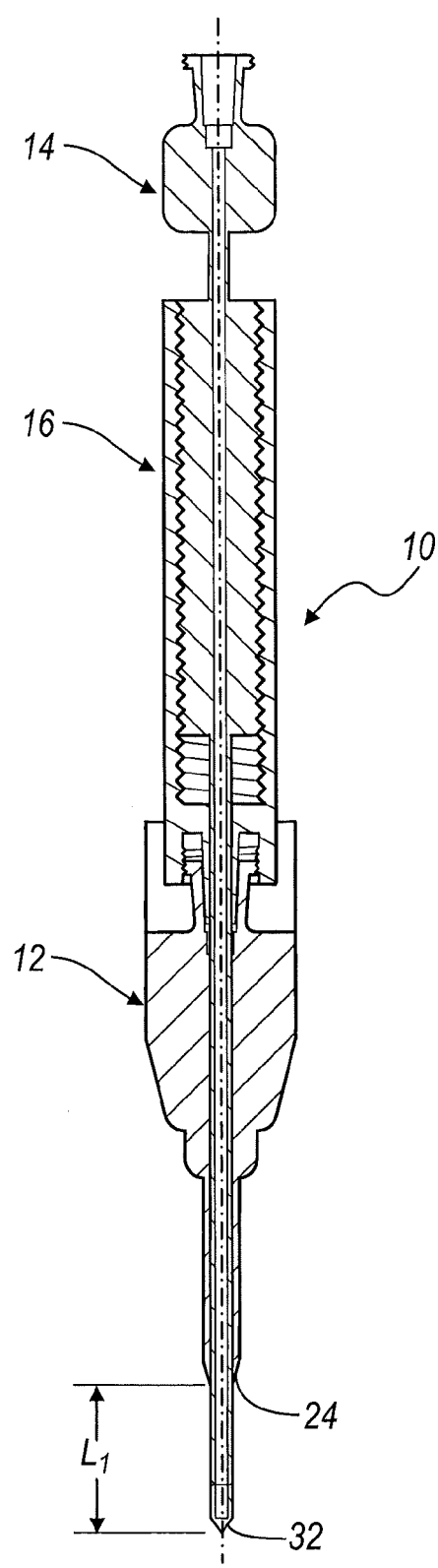
FIG. 7A is a cross-sectional view of the aspiration needle assembly with the inner aspiration needle in a first position in which the inner aspiration needle extends a first length L1 beyond the tip of the outer needle.

The stylet 48 is removed and the threaded collar 16 is attached to the handle 18. Specifically, the male Luer lock 38 of the threaded collar 16 is attached to the female Luer lock 20 of the handle 18 by inserting the outer cylindrical sidewall 21 of the female Luer lock 20 within the recessed portion 44 of the male Luer lock 38 so that the threads 45 engage the threaded second diameter portion 21b of the sidewall 21. The aspiration needle 14 is inserted through the threaded collar 16 and the outer needle 12 such that the tip portion 32 extends out through and beyond the tip portion 24 and the threaded portion 28 threadably mates with the threads 40 of the threaded collar 16. Positioning the inner aspiration needle 14, as illustrated in FIG. 7A, allows the tip 32 of the inner aspiration needle 14 to protrude from the outer needle 12 to a first length L1, which is far enough from the needle portion 22 of the outer needle 12 to aspirate the first two to three milliliters of bone marrow.

Bone marrow is aspirated by attaching a suitable device, such as a syringe, to the female Luer lock 26 of the inner aspiration needle 14. The presence of the ports 34 at the tip 32 facilitates aspiration of bone marrow through the inner aspiration needle 14 from the area surrounding the tip 32.

Figure 7B:
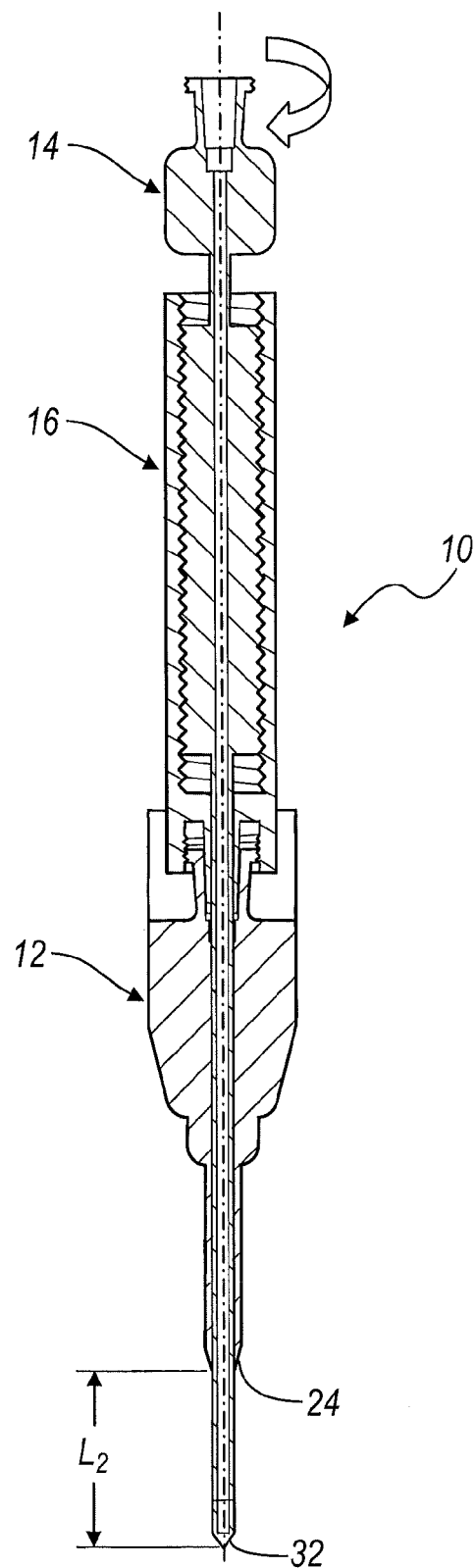
FIG. 7B is a cross-sectional view of the aspiration needle assembly with the inner aspiration needle in a second position in which the inner aspiration needle extends a second length L2 beyond the tip of the outer needle.

To aspirate additional bone marrow, the inner aspiration needle 14 is threaded further into the threaded collar 16 a predetermined number of degrees, such as about 90°, so that the inner aspiration needle 14 protrudes from the outer needle 12 to a second length L2 (FIG. 7B), which is greater than the first length L1. Rotating the inner aspiration needle 14 in this manner, while keeping the outer needle 12 stationary, advances the tip 32 of the needle 30 deeper into the bone and rotates the tip 32 such that the ports 34 are perpendicular to their previous position. Thus, the outer needle 12 serves as a guide for the inner aspiration needle 14 to direct the inner aspiration needle 14 to the bone. This process is performed as many times as needed to obtain a desired amount of bone marrow.

Withdrawing bone marrow using the assembly 10 provides numerous advantages. For example, rotating the inner aspiration needle 14 so that its position in the bone changes permits withdrawal of bone marrow from different areas of the bone to prevent the aspirated marrow from possibly being diluted with peripheral blood.

As an alternative to advancing the inner aspiration needle 14 into the bone as additional bone marrow is withdrawn, bone marrow aspiration can begin with the threaded portion 28 of the inner aspiration needle 14 in full threaded engagement with the threaded collar 16. As additional bone marrow is aspirated, the inner aspiration needle 14 can be rotated, for example counterclockwise at 90°, to withdraw the inner aspiration needle 14 out from within the outer needle 12.

Further, any suitable metering device that provides control over the distance that the inner aspiration needle 14 extends from the outer needle 12 may be used in place of the threaded collar 16. For example, a collar having a series of spaced apart notches for cooperating with tabs spaced apart on the inner aspiration needle 14 can be used. Further, in place of the threaded portion 28 and the threaded sidewall 40 can be opposing surfaces with any suitable friction generating surface so as to provide control over the distance that the inner aspiration needle 14 extends from the outer needle 12.

Figure 8A:
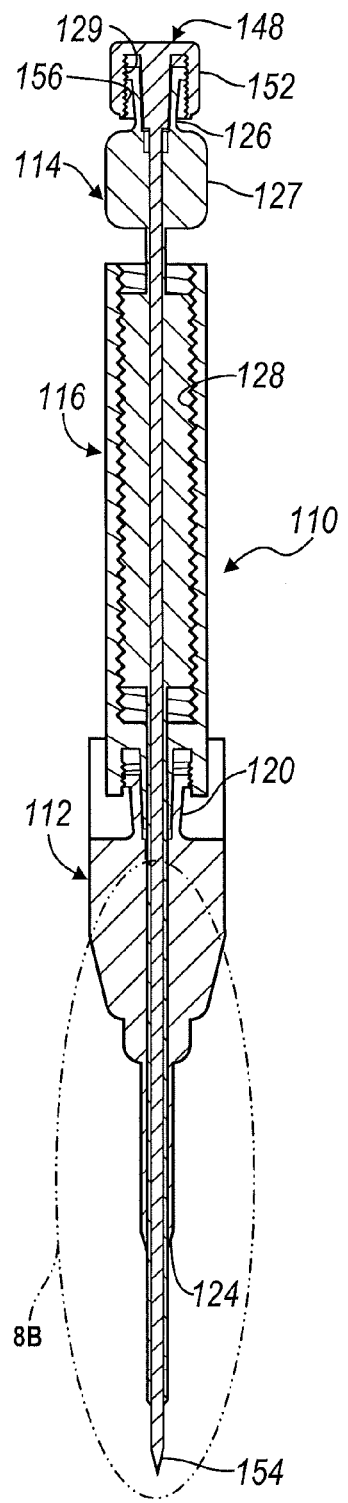
FIG. 8A is a cross-sectional view of an additional aspiration assembly according to the present teachings.
Figure 8C:
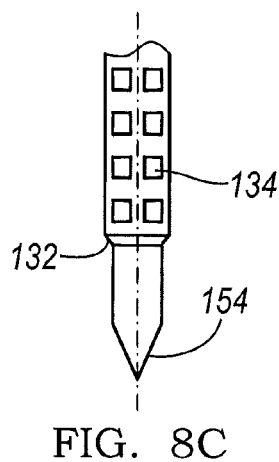
FIG. 8C is a close-up view of a tip portion of the aspiration assembly of FIG. 8A.
Figure 8B:
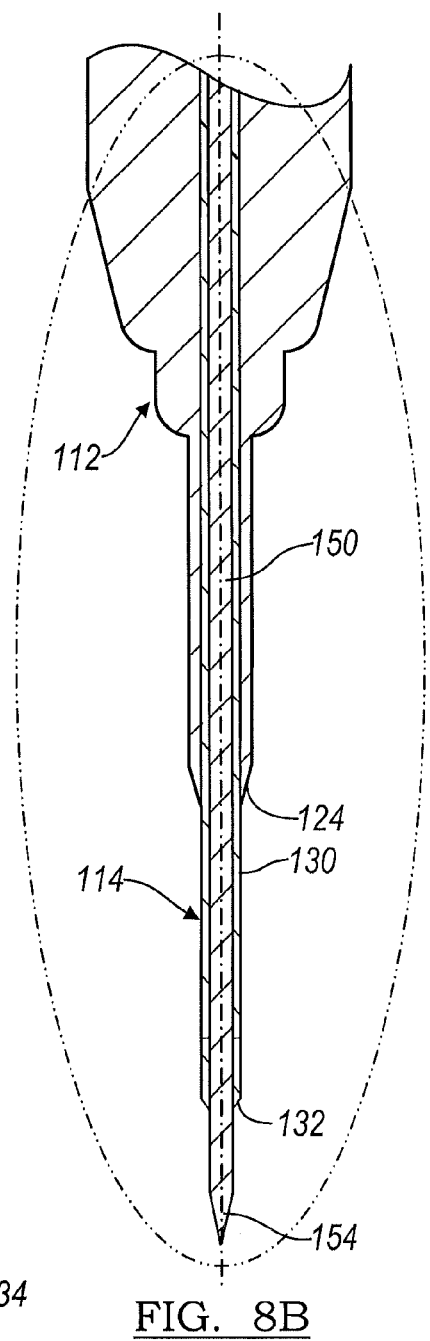
FIG. 8B is a close-up view of area 8B of FIG. 8A.

An additional bone marrow aspiration needle assembly is illustrated in FIGS. 8A, 8B, and 8C at reference numeral 110. The assembly 110 is similar to the assembly 10. As such, similar features are designated using like reference numbers, but increased by 100. With respect to such similar features, the above description of the assembly 10 also applies to the assembly 110.

As with the assembly 10, the assembly 110 generally includes an outer needle 112, an inner needle 114, a threaded collar 116, and a stylet 148. However, unlike the inner needle 14 of the assembly 10, the inner needle 114 of the assembly 110 is cannulated across its entire length. The cannulated inner needle 114 includes a handle portion 127, a Luer lock connector 126, a threaded portion 128, a needle portion 130, an open tip 132, and a plurality of ports 134 (FIG. 8C) around its outer diameter proximate to the open tip 132.

The assembly 110 further includes a stylet 148. The stylet 148 generally includes a rigid needle portion 150 having an end cap 152 at one end and a needle tip 154 at an opposite end. The end cap 152 includes a Luer lock having threads 156 for connecting the stylet 148 to external threads 129 of the Luer lock 126 of the inner needle 114, as illustrated in FIGS. 8A and 8B. The needle portion 150 of the stylet 148 is of a sufficient length such that the tip 154 extends beyond the tip 132 of the inner needle 114 when the stylet 148 is mounted to the inner needle 114.

With the stylet 148 mounted to the inner needle 114 and extending there through, the assembly 110 can be inserted directly into the bone cortex in the same manner described above with respect to the assembly 10, a difference being that the inner needle 114 is inserted together with the stylet 148 and the outer needle 112. Because the tip 154 of the stylet 148 extends beyond the tip 132 of the inner needle 114, it is the stylet 148 that first penetrates the bone cortex.

After the assembly 110 is inserted into the bone cortex, the stylet 148 is removed from cooperation with the inner needle 114 and a suitable device, such as a syringe, is attached to the Luer lock 126 of the inner needle 114 to aspirate bone marrow. The assembly 110 is then used to aspirate bone marrow in a similar manner as described above with respect to the use of the assembly 10. Thus, with the assembly 110 the cannulated inner needle 114 and the threaded collar 116 can both be mounted to the outer needle 112 prior to insertion of the assembly 110 into the bone cortex.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An aspiration assembly comprising:
    an outer cannulated needle having a first tip at a first end and a first coupling device at a second end that is opposite to the first end;
    a threaded collar having a second coupling device in cooperation with the first coupling device to removably couple the threaded collar to the outer cannulated needle; and
    an inner aspiration needle having a second tip at a third end, a third coupling device at a fourth end opposite to the third end, and a threaded portion proximate to the fourth end;
    wherein the inner aspiration needle is inserted within the outer cannulated needle such that the second tip of the inner aspiration needle extends beyond the first tip of the outer cannulated needle and the threaded portion of the inner aspiration needle threadably engages the threaded collar;
    wherein the distance that the second tip of the inner aspiration needle extends from the first tip of the outer cannulated needle increases when the inner aspiration needle is rotated in a first direction relative to the outer cannulated needle; and
    wherein the distance that the second tip of the inner aspiration needle extends from the first tip of the outer cannulated needle decreases when the inner aspiration needle is rotated in a second direction relative to the outer cannulated needle, the second direction is opposite to the first direction.

2. The aspiration assembly of claim 1, wherein the outer cannulated needle further includes a handle proximate to the second end.

3. The aspiration assembly of claim 1, wherein the first tip of the outer cannulated needle is pointed.

4. The aspiration assembly of claim 1, wherein the threaded collar is mounted to the outer cannulated needle with a Leur lock.

5. The aspiration assembly of claim 1, wherein the threaded collar includes internal threads.

6. The aspiration assembly of claim 1, wherein the second tip of the inner aspiration needle includes a plurality of ports spaced apart around an outer circumference of the needle adjacent to the second tip.

7. The aspiration assembly of claim 1, wherein the inner aspiration needle includes a Luer lock attachment at the fourth end to permit cooperation with an aspiration syringe.

8. The aspiration assembly of claim 1, wherein the inner aspiration needle is cannulated; and
    wherein the third coupling device includes a Luer lock attachment configured to cooperate with a stylet, a third tip of the stylet extends beyond the second tip of the inner aspiration needle when the stylet is inserted within the inner aspiration needle and the Luer lock attachment of the stylet is connected to the inner aspiration needle.

9. The aspiration assembly of claim 1, wherein the first coupling device is substantially similar to the third coupling device.

10. An aspiration assembly comprising:
    an outer cannulated needle having a first tip at a first end, a first coupling device at a second end that is opposite to the first end, and a handle;
    a collar having first internal threads and a second coupling device having second internal threads that are spaced apart from and discontinuous with the first internal threads, the second coupling device is configured to cooperate with the first coupling device to removably couple the collar to the outer cannulated needle;
    an inner aspiration needle having a second tip at a third end, a third coupling device substantially similar to the first coupling device at a fourth end opposite to the third end, a threaded portion proximate to the fourth end, and a first needle portion between the second tip of the inner aspiration needle and the fourth end of the inner aspiration needle, the threaded collar is configured to entirely receive the threaded portion; and
    a rigid stylet having a third tip at a fifth end, an interlocking device at a sixth end that is configured to independently cooperate with each of the first coupling device and the third coupling device, and a second needle portion extending between the third tip of the stylet and the interlocking device;
    wherein the assembly includes a first configuration in which the rigid stylet mates with the first coupling device of the outer cannulated needle, the second needle portion of the stylet extends through the needle first tip of the outer cannulated needle, and the third tip of the rigid stylet extends beyond the first tip of the outer cannulated needle; and
    wherein the assembly includes a second configuration in which the collar is mounted to the first coupling device of the outer cannulated needle, the inner aspiration needle is connected to the collar through cooperation between the first internal threads of the collar and the threaded portion of the inner aspiration needle such that an entirety of the threaded portion engages the first internal threads, the first needle portion of the inner aspiration needle extends through the first tip of the outer cannulated needle, and the second tip of the inner aspiration needle extends beyond the first tip of the outer cannulated needle.

11. The aspiration assembly of claim 10, wherein the distance that the second tip of the inner aspiration extends from the needle first tip of the outer cannulated needle increases when the inner aspiration needle is rotated with respect to the outer cannulated needle.

12. The aspiration assembly of claim 10, wherein the collar is mounted to the handle with a Luer lock.

13. The aspiration assembly of claim 10, wherein the second tip of the inner aspiration needle includes a plurality of ports spaced apart around an outer surface of the second tip.

14. The aspiration assembly of claim 10, wherein the inner aspiration needle includes a Luer lock attachment at the fourth end to permit cooperation with an aspiration syringe.

15. The aspiration assembly of claim 10, wherein the handle defines a recess for a Luer lock.

16. The aspiration assembly of claim 10, wherein the collar is one of integral with the outer cannulated needle or removably mounted to the outer cannulated needle.

17. An aspiration assembly comprising:
   an outer cannulated needle having a first tip at a first end, a first coupling device at a second end that is opposite to the first end, and a handle;
   a collar having first internal threads and a second coupling device having second internal threads that are spaced apart from and discontinuous with the first internal threads, the second coupling device is configured to cooperate with the first coupling device to removably couple the collar to the outer cannulated needle;
   an inner aspiration needle having an open second tip at a third end, a connection device at a fourth end that is opposite to the third end, a threaded portion proximate to the fourth end, and a first needle portion between the second tip of the inner aspiration needle and the fourth end of the inner aspiration needle; and
   a stylet having a third tip at a fifth end, an interlocking device at a sixth end, and a second needle portion extending between the third tip of the stylet and the interlocking device;
   wherein the collar is mounted to the first coupling device of the outer cannulated needle;
   wherein the inner aspiration needle is connected to the collar through cooperation between the first internal threads of the collar and an entirety of the threaded portion of the inner aspiration needle, the first needle portion of the inner aspiration needle extends through the needle first tip of the outer cannulated needle, and the second tip of the inner aspiration needle extends beyond the first tip of the outer cannulated needle; and
   wherein the stylet is connected to the inner aspiration needle through cooperation between the interlocking device of the stylet and the connection device of the inner aspiration needle, the second needle portion of the stylet extends through the open second tip of the inner aspiration needle and the third tip of the stylet extends beyond the open second tip of the inner aspiration needle.

18. The aspiration assembly of claim 17, wherein the stylet is rigid.

19. The aspiration assembly of claim 17, wherein the distance that the second tip of the inner aspiration needle extends from the first tip of the outer cannulated needle increases when the inner aspiration needle is rotated with respect to the outer cannulated needle.

20. The aspiration assembly of claim 17, wherein the collar is mounted to the handle with a Luer lock.

21. The aspiration assembly of claim 17, wherein the connection device of the inner aspiration needle includes a Luer lock attachment to permit cooperation with an aspiration syringe.

22. The aspiration assembly of claim 17, wherein the handle defines a recess for a Luer lock.

23. An aspiration assembly comprising:
   an outer cannulated needle having an open tip including:
      a first locking device longitudinally aligned with the open tip, the first locking device including first external threads;
      a handle between the open tip and the first locking device; and
      an outer passageway defined by a body of the outer cannulated needle that extends from the open tip to the first locking device and entirely through the first locking device;
   a collar including:
      a first end and a second end opposite to the first end;
      a bore defined by the collar that extends between the first end and the second end, the bore includes:
         a first bore portion including first internal threads proximate to the first end and a first diameter portion; and
         a second bore portion that is non-threaded and proximate to the second end that has a second diameter that is smaller than the first diameter;
      a second locking device at the second end configured to cooperate with the first locking device to secure the collar to the outer cannulated needle, the second locking device includes:
         a recessed portion that surrounds the second bore portion and is recessed within the second end; and
         second internal threads within the recessed portion that are configured to cooperate with the first external threads of the first locking device;
      a port extension at an axial center of the recessed portion that extends beyond the second end of the collar, the port extension defines a portion of the second bore portion;
   an inner aspiration needle including:
      a third locking device at a third end, the third locking device includes second external threads and is substantially similar to the first locking device;
      a closed, pointed tip at a fourth end that is opposite to the third end;
      an inner passageway defined by an inner body of the inner aspiration needle that extends from about the third end to the fourth end, the inner passageway terminates at an opening defined by the third locking device;
      a plurality of ports proximate to the pointed tip to provide fluid communication between the ports and the third end; and
      a threaded portion between the third end and the fourth end, the threaded portion is configured to cooperate with, and be entirely received by, the threaded bore of the collar; and
   a rigid stylet having a closed stylet tip at a fifth end and a fourth locking device at a sixth end that is opposite to the fifth end, the fourth locking device includes a cap with internal threads, the fourth locking device is configured to independently cooperate with each one of the third locking device of the inner aspiration needle and the first locking device of the outer cannulated needle.

24. The aspiration assembly of claim 23, wherein the collar is coupled to the outer cannulated needle and the inner aspiration needle is inserted within the outer cannulated needle such that the closed, pointed tip of the inner aspiration needle extends beyond the open tip of the outer cannulated needle and the second internal threads of the inner aspiration needle threadably engage the second internal threads of the collar.

25. The aspiration assembly of claim 24, wherein a distance that the closed, pointed tip of the inner aspiration needle extends from the open tip of the outer cannulated needle increases when the inner aspiration needle is rotated in a first direction relative to the outer cannulated needle; and wherein the distance that the closed, pointed tip of the inner aspiration needle extends from the open tip of the outer cannulated needle decreases when the inner aspiration needle is rotated in a second direction that is opposite to the first direction.

26. The aspiration assembly of claim 23, wherein rigid stylet is mounted to one of the third locking device of the inner aspiration needle or the first locking device of the outer cannulated needle such that the closed stylet tip extends through the open tip of the outer cannulated needle.

27. The aspiration assembly of claim 23, wherein the first locking device includes a Luer lock and the third locking device includes a Luer lock.

28. The aspiration assembly of claim 23, wherein the plurality of ports of the inner aspiration needle are spaced apart around an outer circumference of the inner aspiration needle 29. The aspiration assembly of claim 23, wherein the third locking device includes a Luer lock attachment configured to cooperate with an aspiration syringe.

30. The aspiration assembly of claim 23, wherein the first locking device of the outer cannulated needle and the second locking device of the collar are unitary.

* * * * *

UNITED STATES PATENT AND TRADEMARK OFFICE
CERTIFICATE OF CORRECTION

| | | |
|---|---|---|
| PATENT NO. | : 7,850,651 B2 | |
| APPLICATION NO. | : 12/210372 | |
| DATED | : December 14, 2010 | |
| INVENTOR(S) | : Allee et al. | |

It is certified that error appears in the above-identified patent and that said Letters Patent is hereby corrected as shown below:

In the Claims

Column 7, line 64, claim 4; "Leur" should be --Luer--

Column 8, line 47, claim 10; delete "needle"

Column 9, line 42, claim 17; delete "needle"

Signed and Sealed this
Fourth Day of March, 2014

Michelle K. Lee
*Deputy Director of the United States Patent and Trademark Office*